United States Patent
Nalesnik et al.

(10) Patent No.: US 6,187,726 B1
(45) Date of Patent: Feb. 13, 2001

(54) SUBSTITUTED LINEAR THIOUREA ADDITIVES FOR LUBRICANTS

(75) Inventors: Theodore E. Nalesnik, Hopewell Junction, NY (US); Franklin H. Barrows, Waterbury, CT (US)

(73) Assignee: CK Witco Corporation, Middlebury, CT (US)

( * ) Notice: Under 35 U.S.C. 154(b), the term of this patent shall be extended for 0 days.

(21) Appl. No.: 09/439,606

(22) Filed: Nov. 12, 1999

(51) Int. Cl.[7] ............... C07C 335/04; C10M 135/16
(52) U.S. Cl. ............... 508/552; 564/17; 564/30; 564/31; 508/376
(58) Field of Search ............... 508/552; 564/17, 564/30, 31

(56) References Cited

U.S. PATENT DOCUMENTS

| | | | |
|---|---|---|---|
| 3,296,136 | * 1/1967 | Eickmeyer et al. | 508/552 |
| 3,584,993 | * 6/1971 | Myles et al. | 508/552 |
| 4,097,605 | * 6/1978 | Fancher | 564/17 |
| 4,240,954 | * 12/1980 | Stretanski | 508/552 |
| 4,261,845 | * 4/1981 | Cuscurida | 508/552 |
| 4,263,154 | 4/1981 | Ryer et al. | 252/47.5 |
| 4,303,539 | * 12/1981 | Song | 508/552 |
| 4,487,783 | * 12/1984 | Grohe et al. | 564/17 |
| 5,032,309 | * 7/1991 | Miles | 508/552 |
| 5,084,195 | 1/1992 | Camenzind et al. | 252/47.5 |
| 5,300,243 | 4/1994 | Camenzind et al. | 252/47.5 |
| 5,370,947 | * 12/1994 | Uemachi et al. | 564/17 |
| 5,498,809 | 3/1996 | Emert et al. | 585/13 |
| 5,512,190 | 4/1996 | Anderson et al. | 252/47 |
| 5,514,189 | 5/1996 | Farng et al. | 44/383 |
| 5,935,913 | 8/1999 | Nalesnik et al. | 508/225 |

* cited by examiner

*Primary Examiner*—Ellen M. McAvoy
(74) *Attorney, Agent, or Firm*—Raymond D. Thompson; Paul Grandinetti

(57) ABSTRACT

Compounds and lubricant compositions are disclosed that comprise a substituted linear thiourea of the structure

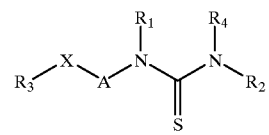

wherein $R_1$, $R_2$, and $R_4$ are independently selected from the group consisting of alkyl, alkenyl, aryl, alkaryl, aralkyl, and hydrogen; $R_3$ is selected from the group consisting of alkyl, alkenyl, and combinations thereof; X is selected from the group consisting of (i) methylene, if, and only if, $R_3$ is alkenyl, (ii) oxygen, and (iii) sulfur; and A is selected from the group consisting of alkylene and aryl.

23 Claims, No Drawings

SUBSTITUTED LINEAR THIOUREA ADDITIVES FOR LUBRICANTS

BACKGROUND OF THE INVENTION

1. Field of the Invention

The present invention relates to lubricants, especially lubricating oils, and, more particularly, to a class of ashless and phosphorus-free, antiwear, anti-fatigue, and extreme pressure additives therefor derived from substituted linear thioureas.

2. Description of Related Art

In developing lubricants, there have been many attempts to provide additives that impart anti-fatigue, anti-wear, and extreme pressure properties thereto.

Zinc dialkyldithiophosphates (ZDDP) have been used in formulated oils as anti-wear additives for more than 50 years. However, zinc dialkyldithiophosphates give rise to ash, which contributes to particulate matter in automotive exhaust emissions. Regulatory agencies are seeking to reduce emissions of zinc into the environment. In addition, the phosphorus is also suspected of limiting the service life of the catalytic converters that are used on cars to reduce pollution. It is important to limit the particulate matter and pollution formed during engine use for toxicological and environmental reasons, but it is also important to maintain undiminished the anti-wear properties of the lubricating oil.

In view of the aforementioned shortcomings with the known zinc and phosphorus-containing additives, efforts have been made to provide lubricating oil additives that contain neither zinc nor phosphorus.

U.S. Pat. No. 5,935,913 discloses a composition comprising:

(A) a lubricant, and
(B) at least one cyclic thiourea selected from the group consisting of:

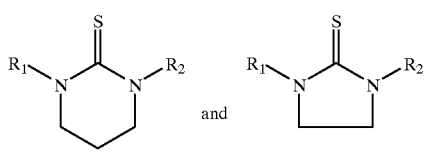

wherein $R_1$ and $R_2$ are independently selected from the group consisting of alkyl, functionalized alkyl, and hydrogen.

Illustrative of non-zinc, i.e., ashless, non-phosphorus-containing lubricating oil additives are the reaction products of 2,5-dimercapto-1,3,4-thiadiazoles and unsaturated mono-, di-, and tri-glycerides of U.S. Pat. No. 5,512,190 and the dialkyl dithiocarbamate-derived organic ethers of U.S. Pat. No. 5,514,189.

U.S. Pat. No. 5,512,190 discloses an additive that provides antiwear properties to a lubricating oil. The additive is the reaction product of 2,5-dimercapto-1,3,4-thiadiazole and a mixture of unsaturated mono-, di-, and triglycerides. Also disclosed is a lubricating oil additive with antiwear properties produced by reacting a mixture of unsaturated mono-, di-, and triglycerides with diethanolamine to provide an intermediate reaction product and reacting the intermediate reaction product with 2,5-dimercapto-1,3,4 thiadiazole.

U.S. Pat. No. 5,514,189 discloses that dialkyl dithiocarbamate-derived organic ethers have been found to be effective antiwear/antioxidant additives for lubricants and fuels.

U.S. Pat. No. 5,498,809 discloses oil soluble copolymers derived from ethylene and 1-butene that have a number average molecular weight between about 1,500 and 7,500, at least about 30 percent of all polymer chains terminated with ethylvinylidene groups, and an ethylene-derived content of not greater than about 50 weight percent, and which form solutions in mineral oil free of polymer aggregates, as determined by light scattering measurements. Lubricating oil additives, particularly dispersants, produced by the functionalization and derivatization of these copolymers are said to have enhanced performance (e.g., improved dispersancy and pour point) in lubricating oil compositions, attributable in part to the combination of properties characterizing the copolymers.

U.S. Pat. Nos. 5,084,195 and 5,300,243 disclose N-acyl-thiourethane thioureas as antiwear additives specified for lubricants or hydraulic fluids.

U.S. Pat. No. 4,303,539 discloses thiocarbamyl derivatives, including thioureas and thiocarbamic esters derived from the reaction of an alkenyl isothiocyanate with an amine and alcohol or thio, respectively, have utility as an additive for hydrocarbons, particularly fuels and mineral lubricating oils whereby enhanced anticorrosion, oxidation inhibition and/or dispersancy activity is imparted to said hydrocarbons.

U.S. Pat. No. 4,263,154 discloses hydrocarbon-soluble sulfur-nitrogen compound resulting from the reaction of a dialkyl-4-hydroxy benzyl thiocyanate and a $C_{12}$–$C_{24}$ alkyl primary amine which compounds have utility as multifunctional, i.e. antioxidation, antiwear, extreme pressure and lubricity modification, additive for fuels and lubricants.

The disclosures of the foregoing references are incorporated herein by reference in their entirety.

SUMMARY OF THE INVENTION

This invention relates to substituted linear thiourea compounds of the formula

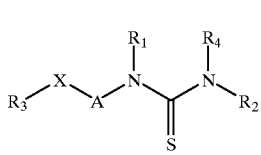

Formula I wherein $R_1$, $R_2$, and $R_4$ are independently selected from the group consisting of alkyl, alkenyl, aryl, alkaryl, aralkyl, and hydrogen and $R_3$ is a linear or branched alkyl or alkenyl group, preferably of from 1 to about 40 carbon atoms, more preferably of from about 8 to about 30 carbon atoms, or a combination of alkyl and alkenyl groups. X can be methylene if $R_3$ is alkenyl (e.g., an oleyl group), otherwise it is oxygen or sulfur, preferably oxygen. A is a branched or straight chained alkylene group or an aryl group, but is preferably ethylene or propylene, more preferably propylene.

The properties of the novel reaction product are also unique in that these linear thioureas are preferably based on or derived from an alkyl ether side chain that enables the additive to be soluble in fully formulated crankcase oil based on mineral and group II, III, and IV base oils, which is not possible with the corresponding purely hydrocarbon side chain (or X=methylene). They can also be used in combination with other additives typically found in motor oils as well as with other ashless anti-wear additives. The typical additives found in motor oils are dispersants, detergents, rust inhibitors, antioxidants, antifoamants, friction modifiers, VI improvers, and pour point depressants.

DESCRIPTION OF THE PREFERRED EMBODIMENTS

In the above structural formula, $R_1$, $R_2$, and $R_4$ are independently selected from the group consisting of alkyl, alkenyl, aryl, alkaryl, aralkyl, and hydrogen. Where at least one of them is alkyl, alkenyl, alkaryl, or aralkyl, the alkyl or alkenyl moiety is preferably of from 1 to 10 carbon atoms, and can be either a straight chain or a branched chain, e.g., methyl, ethyl, propyl, butyl, pentyl, hexyl, 2-ethylhexyl, heptyl, octyl, nonyl, decyl, undecyl, dodecyl, and isomers and mixtures thereof. Where at least one of $R_1$, $R_2$, and $R_4$ is aryl, alkaryl, or aralkyl, the aryl moiety is preferably of from 1 to 12 carbon atoms, e.g., phenyl, naphthyl, anthracyl, phenanthryl, and the like, more preferably phenyl or naphthyl, most preferably phenyl.

$R_3$ can be an alkyl or alkenyl moiety, preferably of from 1 to 40 carbon atoms, and can have either a straight chain or a branched chain, a fully saturated or partially unsaturated hydrocarbon chain and contained within these chains may be ester groups or hetero atoms, such as, oxygen and sulfur, which may take the form of ethers, polyethers, and sulfides, e.g. methyl, ethyl, propyl, butyl, pentyl, hexyl, 2-ethylhexyl, heptyl, octyl, nonyl, decyl, undecyl, dodecyl, tridecyl, tetradecyl, pentadecyl, hexadecyl, heptadecyl, octadecyl, oleyl, nonadecyl, eicosyl, heneicosyl, docosyl, tricosyl, tetracosyl, pentacosyl, triacontyl, pentatriacontyl, tetracontyl, and the like, and isomers and mixtures thereof.

X can be methylene if $R_3$ is alkenyl (e.g., an oleyl group), otherwise it is oxygen or sulfur, preferably oxygen.

A is a branched or straight chained alkylene or an aryl group, preferably propylene or ethylene.

The substituted linear thiourea compounds of this invention are useful as ashless and phosphorus-free anti-fatigue, anti-wear, and extreme pressure additives for lubricants, especially lubricating oils.

The present invention also relates to a lubricant composition comprising a lubricant and a functional property-improving amount of at least one substituted linear thiourea compound of Formula I:

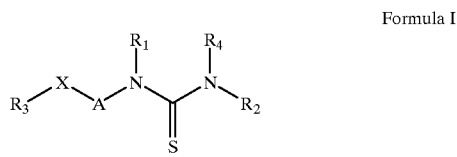

Formula I wherein $R_1$, $R_2$, $R_3$, $R_4$, X, and A are as described above.

In addition to derivatizing ether amines (commercially available from Tohma Products) with alkylisothiocyanates, two equivalents of alkyl isothiocyanates can also be reacted with ether diamines such as the Tohma ether diamine "DA" series or Akzo Duomeen (non-ether) series, to make the corresponding bis-thioureas. These materials also demonstrate active antiwear properties as shown in Example 3.

The functional properties of a lubricant that can be improved by the use of the substituted linear thiourea compounds of the present invention include anti-fatigue, anti-wear, and extreme pressure properties.

The preferred synthesis of the N-substituted linear thioureas of the present invention is carried out by the reaction of an alkyloxypropyl amine with, preferably, methylisothiocyanate to form the N-alkyloxypropyl-N-methyl thiourea product.

In this reaction, a variety of solvents can be used provided they are inert toward reactions with the alkyl isothiocyanate, e.g., methylisothiocyanate, under the reaction conditions. Such solvents include secondary alcohols (e.g., isopropyl alcohol or sec-butyl alcohol); linear, branched, or cyclic hydrocarbons (e.g., hexane, heptane, cyclohexane, or mixtures thereof); aromatic or alkylaromatic hydrocarbons (e.g., benzene, toluene, xylenes, or tetralins); and petroleum mineral oils or synthetic oils (e.g., poly α-olefins or polyol ester oils). The reaction process may require a single or mixed solvent, of which one or all may be removed from the product or remain as part of the product's commercial composition. The final product may be isolated neat or diluted in a solvent.

The reaction is carried out by the slow addition of alkyl isothiocyanate, e.g., methylisothiocyanate, to the substituted amine in the appropriate solvent under an inert atmosphere, such as nitrogen. The reaction is very exothermic, forming the N-alkyloxypropyl-N'-methyl thiourea product. The temperature of the reaction should be kept below 40° C., preferably in the range of from about 20° to about 30° C. The reaction can be cooled by use of a cooling jacket, coils, an ice-bath, or the like.

It should be noted that any alcoholic by-products in the starting amine may be converted to N-alkyl or methyl thiocarbamates. These thiocarbamates, if formed, also show some antiwear activity, although the effect is relatively weak compared to that of the thioureas.

After the methylisothiocyanate addition is completed, the temperature is slowly raised to 70° to 85° C. and maintained there for one hour. The reaction product is then filtered and stripped of the reaction solvent under vacuum, maintaining the media temperature below 85° C.

The additives of the present invention can be used as either partial or complete replacements for the zinc dialkyldithiophosphates currently used. They can also be used in combination with other additives typically found in lubricants, as well as with other ashless anti-wear additives. Typical additives found in lubricating oils are dispersants, detergents, rust inhibitors, antioxidants, antiwear agents, antifoamants, friction modifiers, seal swell agents, demulsifiers, VI improvers, and pour point depressants. See, e.g., U.S. Pat. No. 5,498,809 for a description of useful lubricating oil composition additives. Examples of these materials include polyisobutylene succinimide dispersants, polyisobutylene succinate ester dispersants, Mannich Base ashless dispersants, metallic phenate detergents, metallic sulfonate detergents, metallic salicylate detergents, alkylated diphenylamine antioxidants, N-alkylated phenylenediamine antioxidants, hindered phenolic antioxidants, alkylated hydroquinones, hydroxylated thiodiphenyl ethers, alkylidenebisphenols, oil soluble copper compounds, organo borates, organo phosphites, organic sulfur-containing compounds, zinc dialkyl dithiophosphates, zinc diaryl dithiophosphates, phosphosulfurized hydrocarbons, fatty acid esters and amides, polysiloxanes, polyoxyalkylene polyols, olefin copolymer VI improvers, dispersant olefin copolymer VI improvers, polymethacrylates, sulfurized fatty acid esters, and the like.

Lubricant Compositions

Compositions, when they contain these additives, are typically blended into the base oil in amounts such that the additives therein are effective to provide their normal attendant functions. Representative effective amounts of such additives are illustrated in TABLE 1.

TABLE 1

| Additives | Preferred Weight % | More Preferrd Weight % |
|---|---|---|
| V.I. Improver | 1–12 | 1–4 |
| Corrosion Inhibitor | 0.01–3 | 0.01–1.5 |
| Oxidation Inhibitor | 0.01–5 | 0.01–1.5 |
| Dispersant | 01.–10 | 0.1–5 |
| Lube Oil Flow Improver | 0.01–2 | 0.01–1.5 |
| Detergent/Rust Inhibitor | 0.01–6 | 0.01–3 |
| Pour Point Depressant | 0.01–1.5 | 0.01–0.5 |
| Antifoaming Agent | 0.001–0.1 | 0.001–0.01 |
| Antiwear Agent | 0.001–5 | 0.001–1.5 |
| Seal Swellant | 0.1–8 | 0.1–4 |
| Friction Modifier | 0.01–3 | 0.01–1.5 |
| Lubricating Base Oil | Balance | Balance |

When other additives are employed, it may be desirable, although not necessary, to prepare additive concentrates comprising concentrated solutions or dispersions of the subject additives of this invention, together with one or more of said other additives (said concentrate when constituting an additive mixture being referred to herein as an additive-package) whereby several additives can be added simultaneously to the base oil to form the lubricating oil composition. Dissolution of the additive concentrate into the lubricating oil can be facilitated by solvents and/or by mixing accompanied by mild heating, but this is not essential. The concentrate or additive-package will typically be formulated to contain the additives in proper amounts to provide the desired concentration in the final formulation when the additive-package is combined with a predetermined amount of base lubricant. Thus, the subject additives of the present invention can be added to small amounts of base oil or other compatible solvents along with other desirable additives to form additive-packages containing active ingredients in collective amounts of, typically, from about 2.5 to about 90 percent, preferably from about 15 to about 75 percent, and more preferably from about 25 percent to 5 about 60 percent by weight additives in the appropriate proportions with the remainder being base oil. The final formulations can typically employ about 1 to 20 weight percent of the additive-package with the remainder being base oil. All of the weight percentages expressed herein (unless otherwise indicated) are based on the active ingredient (AI) content of the additive, and/or upon the total weight of any additive-package, or formulation, which will be the sum of the AI weight of each additive plus the weight of total oil or diluent.

In general, the lubricant compositions of the invention contain the additives in a concentration ranging from about 0.05 to about 30 weight percent. A concentration range for the additives ranging from about 0.1 to about 10 weight percent based on the total weight of the oil composition is preferred. A more preferred concentration range is from about 0.2 to about 5 weight percent. Oil concentrates of the additives can contain from about 1 to about 75 weight percent of the additive reaction product in a carrier or diluent oil of lubricating oil viscosity.

In general, the additives of the present invention are useful in a variety of lubricating oil base stocks. The lubricating oil base stock is any natural or synthetic lubricating oil base stock fraction having a kinematic viscosity at 100° C. of about 2 to about 200 cSt, more preferably about 3 to about 150 cSt, and most preferably about 3 to about 100 cSt. The lubricating oil base stock can be derived from natural lubricating oils, synthetic lubricating oils, or mixtures thereof. Suitable lubricating oil base stocks include base stocks obtained by isomerization of synthetic wax and wax, as well as hydrocrackate base stocks produced by hydrocracking (rather than solvent extracting) the aromatic and polar components of the crude. Natural lubricating oils include animal oils, vegetable oils (e.g., rapeseed oils, castor oils, and lard oil), petroleum oils, mineral oils, and oils derived from coal or shale.

Synthetic oils include hydrocarbon oils and halo-substituted hydrocarbon oils, such as, polymerized and interpolymerized olefins, alkylbenzenes, polyphenyls, alkylated diphenyl ethers, alkylated diphenyl sulfides, as well as their derivatives, analogs, homologues, and the like. Synthetic lubricating oils also include alkylene oxide polymers, interpolymers, copolymers, and derivatives thereof, wherein the terminal hydroxyl groups have been modified by esterification, etherification, etc.

Another suitable class of synthetic lubricating oils comprises the esters of dicarboxylic acids with a variety of alcohols. Esters useful as synthetic oils also include those made from $C_5$ to $C_{12}$ monocarboxylic acids and polyols and polyol ethers.

Silicon-based oils (such as the polyalkyl-, polyaryl-, polyalkoxy-, or polyaryloxy-siloxane oils and silicate oils) comprise another useful class of synthetic lubricating oils. Other synthetic lubricating oils include liquid esters of phosphorus-containing acids, polymeric tetrahydrofurans, poly α-olefins, and the like.

The lubricating oil may be derived from unrefined, refined, rerefined oils, or mixtures thereof. Unrefined oils are obtained directly from a natural source or synthetic source (e.g., coal, shale, or tar and bitumen) without further purification or treatment. Examples of unrefined oils include a shale oil obtained directly from a retorting operation, a petroleum oil obtained directly from distillation, or an ester oil obtained directly from an esterification process, each of which is then used without further treatment. Refined oils are similar to unrefined oils, except that refined oils have been treated in one or more purification steps to improve one or more properties. Suitable purification techniques include distillation, hydrotreating, dewaxing, solvent extraction, acid or base extraction, filtration, percolation, and the like, all of which are well-known to those skilled in the art. Rerefined oils are obtained by treating refined oils in processes similar to those used to obtain the refined oils. These rerefined oils are also known as reclaimed or reprocessed oils and often are additionally processed by techniques for removal of spent additives and oil breakdown products.

Lubricating oil base stocks derived from the hydroisomerization of wax may also be used, either alone or in combination with the aforesaid natural and/or synthetic base stocks. Such wax isomerate oil is produced by the hydroisomerization of natural or synthetic waxes or mixtures thereof over a hydroisomerization catalyst. Natural waxes are typically the slack waxes recovered by the solvent dewaxing of mineral oils; synthetic waxes are typically the wax produced by the Fischer-Tropsch process. The resulting isomerate product is typically subjected to solvent dewaxing and fractionation to recover various fractions having a specific viscosity range. Wax isomerate is also characterized by possessing very high viscosity indices, generally having a VI of at least 130, preferably at least 135 or higher and, following dewaxing, a pour point of about −20° C. or lower.

The additives of the present invention are especially useful as components in many different lubricating oil compositions. The additives can be included in a variety of oils with lubricating viscosity including natural and synthetic lubricating oils and mixtures thereof. The additives can be included in crankcase lubricating oils for spark-ignited and compression-ignited internal combustion engines. The compositions can also be used in gas engine lubricants, turbine lubricants, automatic transmission fluids, gear lubricants, compressor lubricants, metal-working lubricants, hydraulic fluids, and other lubricating oil and grease compositions. The additives can also be used in motor fuel compositions.

The advantages and the important features of the present invention will be more apparent from the following examples.

EXAMPLE 1

(100 wt % active)

Into a one liter flask blanketed with nitrogen is charged 250 grams (1.1 moles) of Tohma PA14 (isodecyloxypropyl amine) and 300 mL of hexane. To this is added, with stirring and external cooling, a solution of 81 grams (1. 1 moles) of methylisothiocyanate in 60 mL of THF at such a rate that the temperature of the reaction, which is exothermal, does not exceed 30° C. The temperature is then slowly raised to reflux and held there for one hour while the reactants are stirred under a nitrogen blanket. The product is cooled, filtered, and stripped of solvent under vacuum to yield a light yellow-colored liquid.

EXAMPLE 2

(100 wt % active)

Into a 100 mL flask blanketed with nitrogen is charged 22.5 grams (0.1 mole) of Tohma PA14 (isodecyloxypropyl amine) and 75 mL of hexane. To this is added in solid form, with stirring and external cooling, 7.3 grams (0.1 mole) of methylisothiocyanate at a rate such that the temperature of the exothermal reaction does not exceed 30° C. The temperature is then slowly raised to reflux and held there for one hour while the reactants are stirred under a nitrogen blanket. The product is cooled, filtered, and stripped of solvent under vacuum, below 60° C., to yield a light yellow-colored liquid.

EXAMPLE 3

(100 wt % active)

Into a 100 mL flask blanketed with nitrogen is charged 16.2 grams (0.05 mole) of Tohma DA16 (isotridecyloxy-1-3-propanediamine) and 50 mL of hexane. To this is added in solid form, with stirring and external cooling, 7.3 grams (0.1 mole) of methylisothiocyanate at a rate such that the temperature of the exothermal reaction does not exceed 30° C. The temperature is then slowly raised to reflux and held there for one hour while the reactants are stirred under a nitrogen blanket. The product is cooled, filtered, and stripped of solvent under vacuum, below 60° C., to yield a light yellow-colored liquid.

EXAMPLE 4

(100 wt % active)

Into a one liter flask blanketed with nitrogen is charged 175 grams (0.66 mole) of Tohma PA17 (isotetradecyloxypropyl amine) and 200 mL of hexane. To this is added, with stirring and external cooling, 90 grams (0.66 mole) of phenylisothiocyanate (liquid) at a rate such that the temperature of the reaction, which is exothermal, does not exceed 30° C. The temperature is then slowly raised to reflux and held there for one hour while the reactants are stirred under a nitrogen blanket. The product is cooled, filtered, and stripped of solvent under vacuum to yield a light yellow-colored liquid.

EXAMPLE 5

(100 wt % active)

Into a 100 mL flask blanketed with nitrogen is charged 3.83 grams (0.017 mole) of Tohma PA-14 (isodecyloxypropyl amine) and 25 mL of hexane. To this is added in solid form, with stirring and external cooling, 2.3 grams (0.017 mole) of phenylisothiocyanate at a rate such that the temperature of the reaction, which is exothermal, does not exceed 30° C. The temperature is then slowly raised to reflux and held there for one hour while the reactants are stirred under a nitrogen blanket. The product is cooled, filtered, and stripped of solvent under vacuum to yield a light yellow-colored liquid.

EXAMPLE 6

(100 wt % active)

Into a 250 mL flask blanketed with nitrogen is charged 79.5 grams (0.30 mole) of Tohma PA17 (isotridecyloxypropyl amine) and 100 mL of hexane. To this is added, with stirring and external cooling, a solution of 22 grams (0.30 mole) of methylisothiocyanate in 25 mL of THF at a rate such that the temperature of the reaction, which is exothermal, does not exceed 30° C. The temperature is then slowly raised to reflux and held there for one hour while the reactants are stirred under a nitrogen blanket. The product is cooled, filtered, and stripped of solvent under vacuum to yield a light yellow-colored liquid.

EXAMPLE 7

(100 wt % active)

Into a 100 mL flask blanketed with nitrogen is charged 5.6 grams (0.02 mole) of Tohma PA18 (tetradecyloxypropyl amine) and 25 mL of hexane. To this is added in solid form, with stirring and external cooling, 1.5 grams (0.02 mole) of methylisothiocyanate at a rate such that the temperature of the exothermal reaction does not exceed 30° C. The temperature is then slowly raised to reflux and held there for one hour while the reactants are stirred under a nitrogen blanket. The product is cooled, filtered, and stripped of solvent under vacuum, below 60° C., to yield a light yellow-colored liquid.

Four-Ball Anti-Wear Testing

The anti-wear properties of the novel reaction product in a fully formulated lubricating oil were determined in the Four-Ball Wear Test under the ASTM D 4172 test conditions. The fully formulated lubricating oils tested also contained 1 wt. % cumene hydroperoxide to help simulate the environment within a running engine. The additives were tested for effectiveness in two motor oil formulations (See description in TABLE 2) and compared to identical formulations with and without any zinc dialkyldithiophosphate. In TABLE 3, the numerical value of the test results (Average Wear Scar Diameter, mm) decreases with an increase in effectiveness.

TABLE 2

SAE 10W-30 Motor Oil Formulations

| Component | Formulation A (wt %) | Formulation B (wt %) |
|---|---|---|
| Solvent Neutral 100 | Balance | Balance |
| Solvent Neutral 150 | 60 | 60 |
| Succinimide Dispersant | 7.5 | 7.5 |
| Overbased Calcium Phenate Detergent | 2.0 | — |
| Overbased Calcium Sulfonate Detergent | — | 2.0 |
| Neutral Calcium Sulfonate Detergent | 0.5 | 0.5 |
| Rust Inhibitor | 0.1 | 0.1 |
| Antioxidant | 0.5 | 0.5 |
| Pour Point Depressant | 0.1 | 0.1 |
| OCP VI Improver | 5.5 | 5.5 |
| Antiwear Additive[1] | 1.0 | 1.0 |

In the case of No anti-wear additive in TABLE 3, solvent neutral 100 is put in its place at 1.0 weight percent. The formulation is treated so that 1 wt % antiwear additive is based upon 100% active material.

TABLE 3

Falex Four-Ball Wear Results

| Compound | Formulation | Wear Scar Diameter, mm |
|---|---|---|
| No antiwear additive | A | 0.93 |
| Zinc dialkyldithiophosphate | A | 0.46 |
| Example 1 | A | 0.60 |
| Example 2 | A | 0.50 |
| Example 3 | A | 0.44 |
| Example 4 | A | 0.48 |
| Example 5 | A | — |
| Example 6 | A | 0.53 |
| Example 7 | A | 0.52 |
| No antiwear additive | B | 0.98 |
| Zinc dialkyldithiophosphate | B | 0.53 |
| Example 1 | B | 0.59 |
| Example 2 | B | 0.50 |
| Example 3 | B | 0.52 |
| Example 4 | B | 0.56 |
| Example 6 | B | 0.46 |
| Example 7 | B | 0.45 |

In view of the many changes and modifications that can be made without departing from principles underlying the invention, reference should be made to the appended claims for an understanding of the scope of the protection to be afforded the invention.

What is claimed is:

1. A composition comprising a substituted linear thiourea of the structure

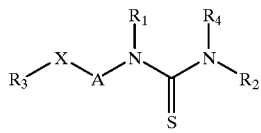

wherein $R_1$, $R_2$, and $R_4$ are independently selected from the group consisting of alkyl, alkenyl, aryl, alkaryl, aralkyl, and hydrogen; $R_3$ is selected from the group consisting of alkyl, alkenyl, and combinations thereof; X is selected from the group consisting of oxygen and sulfur; and A is selected from the group consisting of alkylene and aryl.

2. The composition of claim 1 wherein $R_3$ is alkyl.
3. The composition of claim 2 wherein $R_3$ is isodecyl.
4. The composition of claim 2 wherein $R_3$ is isotridecyl.
5. The composition of claim 2 wherein $R_3$ is isotetradecyl.
6. The composition of claim 2 wherein $R_3$ is tetradecyl.
7. The composition of claim 1 wherein A is propylene.
8. The composition of claim 1 wherein X is oxygen.
9. The composition of claim 1 wherein the substituted linear thiourea is the product of the reaction between an amine selected from the group consisting of isodecyloxypropyl amine, isotridecyloxy-1-3-propanediamine, isotetradecyloxypropanyl amine, and tetradecyloxypropyl amine with an isothiocyanate selected from the group consisting of methylisothiocyanate and phenylisothiocyanate.

10. A composition comprising:
(A) a lubricant, and
(B) at least one a substituted linear thiourea of the structure

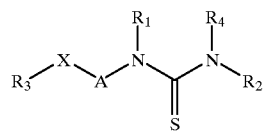

wherein $R_1$, $R_2$, and $R_4$ are independently selected from the group consisting of alkyl, alkenyl, aryl, alkaryl, aralkyl, and hydrogen; $R_3$ is selected from the group consisting of alkyl, alkenyl, and combinations thereof; X is selected from the group consisting of oxygen and sulfur; and A is selected from the group consisting of alkylene and aryl.

11. The composition of claim 10 wherein the lubricant is a lubricating oil.
12. The composition of claim 11 wherein $R_3$ is alkyl.
13. The composition of claim 12 wherein $R_3$ is isodecyl.
14. The composition of claim 12 wherein $R_3$ is isotridecyl.
15. The composition of claim 12 wherein $R_3$ is isotetradecyl.
16. The composition of claim 12 wherein $R_3$ is tetradecyl.
17. The composition of claim 10 wherein A is propylene.
18. The composition of claim 10 wherein X is oxygen.
19. The composition of claim 10 wherein the substituted linear thiourea is the product of the reaction between an amine selected from the group consisting of isodecyloxypropyl amine, isotridecyloxy-1-3-propanediamine, isotetradecyloxypropanyl amine, and tetradecyloxypropyl amine with an isothiocyanate selected from the group consisting of methylisothiocyanate and phenylisothiocyanate.
20. The composition of claim 10 wherein the substituted linear thiourea is present in a concentration in the range of from about 0.01 to about 10 wt %.
21. The composition of claim 11 further comprising at least one additive selected from the group consisting of dispersants, detergents, corrosion/rust inhibitors, zinc dialkyldithiophosphates, VI improvers, pour point depressants, and antioxidants selected from the group consisting of alkylated diphenylamines and hindered phenols.
22. The composition of claim 10 further comprising zinc dialkyldithiophosphate.
23. The composition of claim 11 further comprising zinc dialkyldithiophosphate.

* * * * *